(12) United States Patent
Aso

(10) Patent No.: US 9,834,089 B2
(45) Date of Patent: Dec. 5, 2017

(54) FUEL TANK STRUCTURE

(71) Applicant: TOYOTA JIDOSHA kABUSHIKI KAISHA, Toyota-shi, Aichi-ken (JP)

(72) Inventor: Shuichi Aso, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 35 days.

(21) Appl. No.: 15/071,922

(22) Filed: Mar. 16, 2016

(65) Prior Publication Data

US 2016/0361992 A1    Dec. 15, 2016

(30) Foreign Application Priority Data

Jun. 12, 2015   (JP) ................... 2015-119045

(51) Int. Cl.
    *B60K 15/03*      (2006.01)
    *G01N 25/00*      (2006.01)

(52) U.S. Cl.
    CPC ............. *B60K 15/03* (2013.01); *G01N 25/00* (2013.01); *B60K 2015/0321* (2013.01); *B60K 2015/03217* (2013.01); *B60K 2015/03414* (2013.01)

(58) Field of Classification Search
CPC ............ B60K 15/03; B60K 2015/0321; B60K 2015/03414; B60K 2015/03217; G01N 25/00
USPC ... 137/206, 207.5, 209, 213, 351, 899.4, 34, 137/338, 590; 123/516, 518
See application file for complete search history.

(56) References Cited

U.S. PATENT DOCUMENTS

| 5,596,971 | A | | 1/1997 | Kidokoro | |
|---|---|---|---|---|---|
| 5,746,186 | A | * | 5/1998 | Kidokoro | B60K 15/03 123/516 |
| 5,925,817 | A | * | 7/1999 | Kidokoro | B60K 15/03 73/40 |
| 5,979,417 | A | * | 11/1999 | Hyodo | B60K 15/03 123/516 |
| 5,979,481 | A | * | 11/1999 | Ayresman | B60K 15/03 137/14 |

FOREIGN PATENT DOCUMENTS

| GB | 794125 A | * | 4/1958 | ............ B60K 15/03 |
|---|---|---|---|---|
| JP | H08-170568 A | | 7/1996 | |
| JP | H11-11167 A | | 1/1999 | |
| JP | 2012-172526 A | | 9/2012 | |

* cited by examiner

*Primary Examiner* — Jessica Cahill
*Assistant Examiner* — Josephine Trinidad-Borges
(74) *Attorney, Agent, or Firm* — Oliff PLC

(57) ABSTRACT

A fuel tank structure includes: a fuel tank that is installed in an automobile and that accommodates fuel; a bag-shaped member that is fixed to a ceiling portion of an interior of the fuel tank, and whose state of contact with a liquid surface of fuel accommodated in the fuel tank is maintained due to the bag-shaped member inflating or deflating in accordance with a height of the liquid surface; a temperature sensor that senses a temperature of the fuel or evaporated fuel that is within the fuel tank; and a cooling wind introducing section that introduces cooling wind into an interior of the bag-shaped member in a case in which the temperature of the fuel or the evaporated fuel detected by the temperature sensor becomes higher than a predetermined temperature.

8 Claims, 4 Drawing Sheets

FUEL TANK STRUCTURE

CROSS-REFERENCE TO RELATED APPLICATION

This application claims priority under 35 USC 119 from Japanese Patent Application No. 2015-119045 filed Jun. 12 2015, the disclosure of which is incorporated by reference herein.

BACKGROUND

Technical Field

The present invention relates to a fuel tank structure.

Related Art

A fuel tank structure, in which an expanding/deflating film that can inflate and deflate is provided within a fuel tank, is disclosed in Japanese Patent Application Laid-Open (JP-A) No. H8-170568 as a fuel tank structure that is installed in an automobile. Further, this JP-A No. H8-170568 discloses a technique in which, by making the pressure within the space that is enclosed by the expanding/deflating film higher than the pressure of fuel vapor, the expanding/deflating film is made to contact the liquid surface of the fuel, and the generation of evaporated fuel is suppressed.

SUMMARY

However, the structure of the above-described publication does not consider a rise in the temperature of the fuel tank interior due to exhaust from the engine, the receiving of heat from the engine compartment, the receiving of heat from the road surface, or the like. Therefore, there are cases in which the pressure of the fuel tank interior becomes high due to an increase in the evaporated fuel (vapor) that accompanies a rise in the temperature of the fuel tank interior, and there is room for improvement from the standpoint of suppressing a rise in pressure of the fuel tank interior.

In view of the above-described circumstances, an object of the present invention is to provide a fuel tank structure that can suppress a rise in pressure of a fuel tank interior that is due to a rise in the temperature of the fuel tank interior.

A fuel tank structure of a first aspect includes: a fuel tank that is installed in an automobile and that accommodates fuel; a bag-shaped member that is fixed to a ceiling portion of an interior of the fuel tank, a state of contact of the bag-shaped member with a liquid surface of fuel accommodated in the fuel tank being maintained due to the bag-shaped member inflating or deflating in accordance with a height of the liquid surface; a temperature sensor that detects a temperature of the fuel or evaporated fuel that is within the fuel tank; and a cooling wind introducing section that introduces cooling, wind into an interior of the bag-shaped member in a case in which the temperature of the fuel or the evaporated fuel detected by the temperature sensor is higher than a predetermined temperature.

In the fuel tank structure of the first aspect, the bag-shaped member is fixed to the upper portion of the fuel tank interior. Further, due to this bag-shaped member inflating or deflating in accordance with the height of the liquid surface of the fuel that is accommodated in the fuel tank, the state of contact with the liquid surface of the fuel is maintained. Namely, if the amount of fuel within the fuel tank becomes low, the height of the liquid surface becomes low, and therefore, the bag-shaped member inflates and the state of contact with the liquid surface of the fuel is maintained. On the other hand, if the amount of fuel becomes great due to refueling or the like, the liquid surface becomes high, and therefore, the bag-shaped member deflates, and the state of contact with the liquid surface is maintained. Due thereto, the generation of evaporated fuel from the liquid surface of the fuel can be suppressed.

Further, the fuel tank structure is provided with the cooling wind introducing section that, in a case in which the temperature of the fuel or the evaporated fuel that is detected by the temperature sensor becomes higher than a predetermined temperature, introduces cooling wind into the interior of the bag-shaped member. Due thereto, in a case in which the temperature of the fuel becomes high, cooling wind is introduced into the interior of the bag-shaped member, and heat of the fuel can be taken away. As a result, the temperature of the fuel can be lowered, and the amount of the evaporated fuel (vapor) within the fuel tank can be reduced. Further, by maintaining the state of contact between the bag-shaped member and the liquid surface of the fuel, heat can be effectively taken away from the fuel.

In a fuel tank structure of a second aspect, in the first aspect, the cooling wind introducing section is structured to include an introducing pipe that introduces air into the bag-shaped member, and a cooling device that cools air that flows through the introducing pipe, and, connected to the bag-shaped member is a lead-out pipe that circulates the cooling wind by leading the cooling wind, that has been introduced into the bag-shaped member from the introducing pipe, to the introducing pipe again.

In the fuel tank structure of the second aspect, air that has been cooled by the cooling device is introduced into the bag-shaped member from the introducing pipe. Then, the cooling wind that has been introduced into the bag-shaped member passes-through the lead-out pipe and is again led to the introducing pipe. By circulating the cooling wind in this way, the temperature of the interior of the bag-shaped member can be maintained at a low temperature, and the temperature of the fuel can be lowered effectively.

In a fuel tank structure of a third aspect, in the first aspect or the second aspect, a deflation limiting member, that limits the bag-shaped member from deflating to less than a predetermined size, is provided at the fuel tank.

In the fuel tank structure of the third aspect, collapsing of the bag-shaped member can be suppressed by the deflation limiting member, and a flow path of the cooling wind can be ensured at the interior of the bag-shaped member.

As described above, in accordance with the fuel tank structure of the first aspect, there is the excellent effect that a use in pressure of a fuel tank interior, that is due to a rise in the temperature of the fuel tank interior, can be suppressed.

In accordance with the fuel tank structure of the second aspect, there is the excellent effect that a rise in pressure of the tank interior can be suppressed effectively.

In accordance with the fuel tank structure of the third aspect, there is the excellent effect that the cooling performance can be maintained good regardless of the height of the liquid surface of the fuel.

BRIEF DESCRIPTION OF THE DRAWINGS

Embodiments of the present invention will be described in detail based on the following figures, wherein.

DETAILED DESCRIPTION

<First Embodiment>

A fuel tank structure relating to a first embodiment is described hereinafter with reference to FIG 1 through FIG 3. Note that arrow UP that is shown appropriately in the respective drawings indicates the upper side of a fuel tank. Further, in the present embodiment, the upper side of the fuel tank and the upper side in the vehicle vertical direction coincide with one another.

Figure 1:
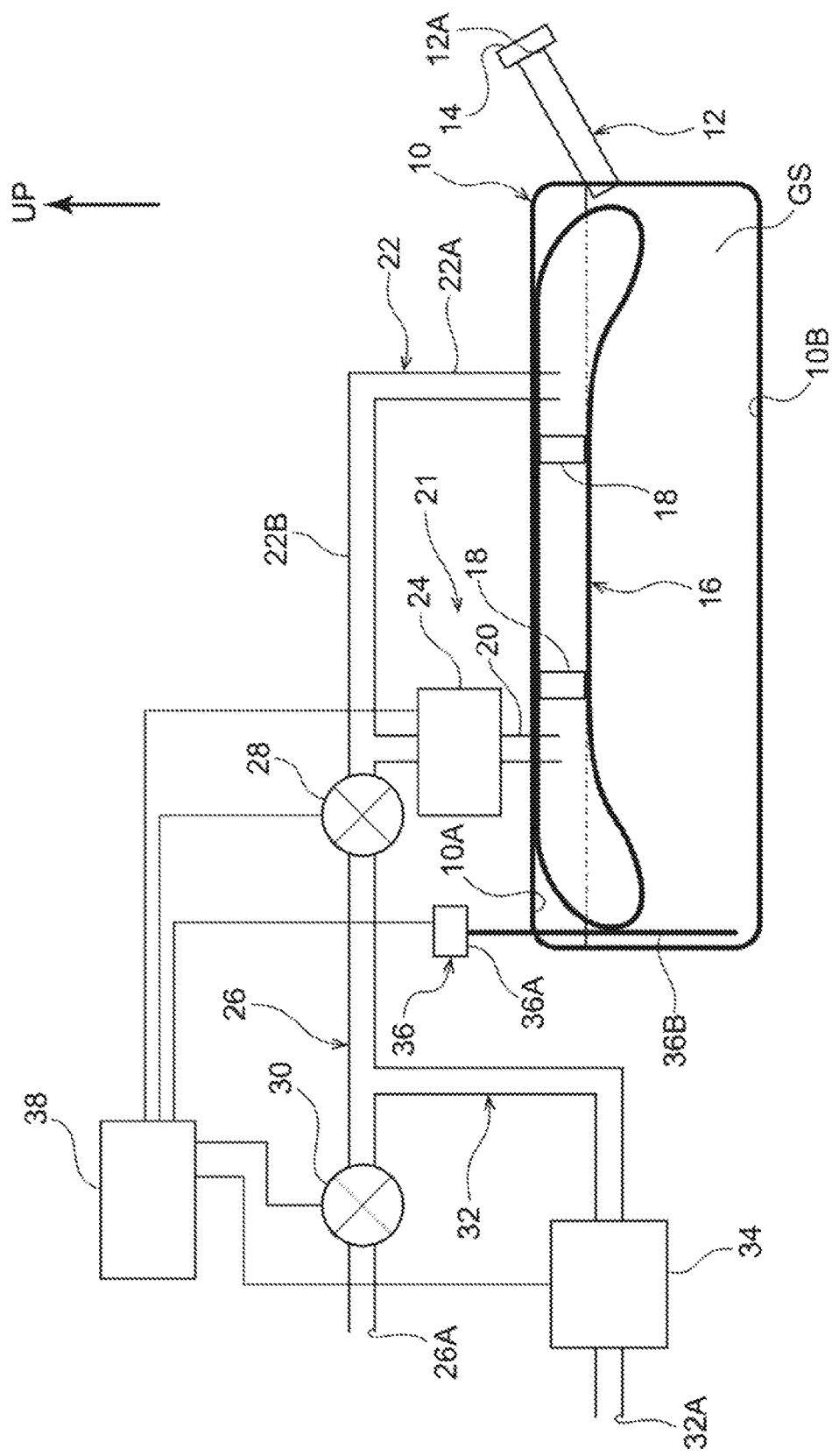
FIG 1 is a drawing that schematically shows the overall structure of a fuel tank structure relating to a first embodiment.
Figure 2:
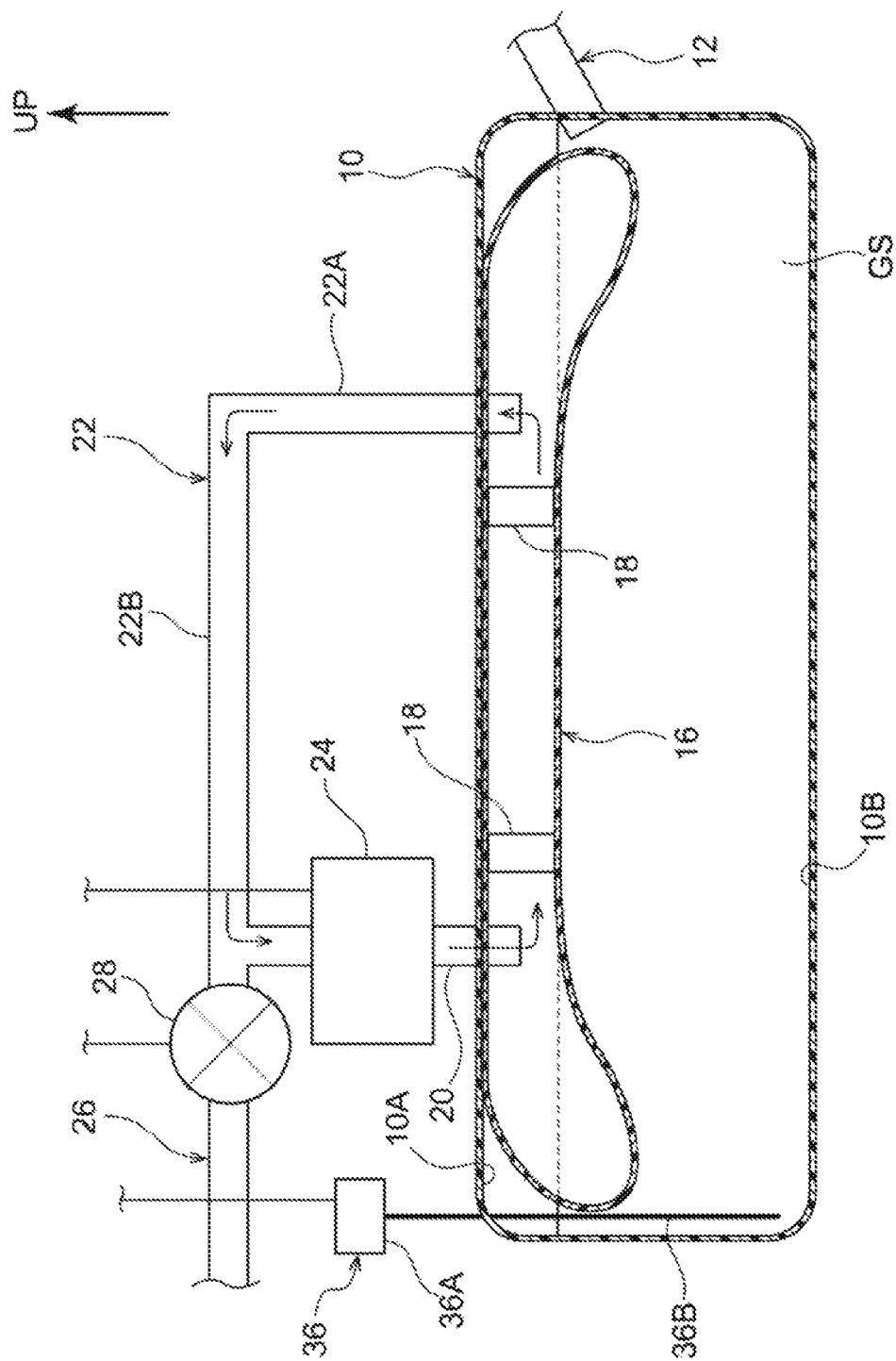
FIG 2 is a cross-sectional view showing main portions of the fuel tank structure relating to the first embodiment, and is a drawing showing a state in which a bag-shaped member is deflated.

As shown in FIG 1, a fuel tank 10, that structures the fuel tank structure relating to the present embodiment, is formed in a hollow shape, and is formed in a shape (e.g., the shape of a substantially parallelepiped box) that can accommodate liquid fuel (hereinafter called "fuel GS") in the interior thereof. Further, the lower surface of the fuel tank 10 is supported by an unillustrated tank band. The fuel tank 10 is mounted to an unillustrated floor panel due to this tank band being fixed to the floor panel via brackets or the like.

A filler pipe 12 that is substantially tubular is connected to the fuel tank 10. A refueling port 12A is formed in the upper end portion of the filler pipe 12. Refueling is carried out due to a refueling gun being inserted into is refueling port 12A and the fuel GS being filled into the fuel tank 10. Note that this is a structure in which, in a case in which there is a large amount of the fuel GS within the fuel tank 10, some of the fuel GS is accommodated in the filler pipe 12 as well.

The refueling port 12A at the upper end of the filler piper 12 is opened and closed by a fuel cap 14. An unillustrated fuel lid, that is provided at a side panel or the like of the vehicle body, is disposed at the outer side of the fuel cap 14.

In the closed state, the fuel cap 14 closes-off the refueling port 12A, and limits access of a refueling gun to the filler pipe 12. In contrast, when the fuel cap 14 is opened, the refueling port 12A of the filler pipe 12 is opened, and access of a refueling gun to the refueling path is possible.

A bag-shaped member 16 and deflation limiting members 18 are provided at a ceiling portion 10A of the fuel tank 10 interior. Details of the bag-shaped member 16 and the deflation limiting members 18 are described later. Further, a detection portion 36B of a temperature sensor 36 is disposed in a vicinity of an inner wall of the fuel tank 10 interior. The temperature sensor 36 is structured to include a main body portion 36A that is disposed at the outer side of the fuel tank 10, and the detection portion 36B that is rod-shaped and that extends downward from the main body portion 36A. Further, the detection portion 36B extends along the inner wall of the fuel tank 10 to a bottom portion 10B, and this is a structure in which the temperature of the fuel GS that is accommodated within the fuel tank 10 can be detected by the detection portion 36B. Note that the temperature sensor is not limited to this, and may be structured so as to sense the temperature of evaporated fuel (vapor).

Here, a cooling wind introducing section 21 is disposed at the ceiling portion 10A of the fuel tank 10. The cooling wind introducing section 21 is structured to include an introducing pipe 20 and a cooling device 24. Further, the cooling device 24 has an unillustrated Peltier element, and is structured such that, in a case in which the temperature of the fuel GS or the temperature of the evaporated fuel that is detected by the temperature sensor 36 is higher than a predetermined temperature (e.g., 30° C.), this Peltier element is energized, and the air that flows within the introducing pipe 20 is cooled.

The introducing pipe 20 is a pipe body for introducing cooling wind into the bag-shaped member 16, and extends in the vertical direction. Further, the lower end portion of the introducing pipe 20 is disposed within the fuel lank 10. On the other hand, the upper end portion of the introducing pipe 20 is connected to the cooling device 24 that structures the cooling wind introducing section 21, and extends further above the cooling device 24 and is connected to a lead-out pipe 22.

The lead-out pipe 22 is a pipe body that leads air out from the bag-shaped member 16, and is structured to include a vertical portion 22A that extends in the vertical direction and a lateral portion 22B that extends substantially horizontally. The lower end portion of the vertical portion 22A is disposed within the fuel tank 10. On the other hand, the upper end portion of the vertical portion 22A is connected to one end portion of the lateral portion 22B. Further, the other end portion of the lateral portion 22B is connected to the upper end portion of the introducing pipe 20.

Here, one end portion of a pipe 26 for opening to the atmosphere is connected to the portion where the introducing pipe 20 and the lead-out pipe 22 are connected. The pipe 26 for opening to the atmosphere extends in a direction of continuing with the lateral portion 22B of the lead-out pipe 22. An opening 26A that opens to the atmosphere is formed at the other end portion of the pipe 26 for opening to the atmosphere. Further, an opening/closing valve 28 and a pressure adjusting valve 30 are provided at the one end side and the other end side, respectively, of the pipe 26 for opening to the atmosphere.

The opening/closing valve 28 is provided in a vicinity of the connected portion of the introducing pipe 20 and the lead-out pipe 22. This is a structure in which, due to the opening/closing valve 28 opening and closing, the entry and exit of air between, on the one hand, the pipe 26 for opening to the atmosphere, and, on the other hand, the introducing pipe 20 and the lead-out pipe 22, can be adjusted.

The pressure adjusting valve 30 is provided in a vicinity of the opening 26A. Further, this is a structure in which, due to the pressure adjusting valve 30 being opened, air within the pipe 26 for opening to the atmosphere is discharged-out into the atmosphere, and the pressure of the pipe 26 for opening to the atmosphere can be adjusted. Note that, in a case in which the opening/closing valve 28 is open, air within the fuel tank 10 is discharged-out into the atmosphere.

One end portion of a branch pipe 32 is connected between the opening/closing valve 28 and the pressure adjusting valve 30 at the pipe 26 for opening to the atmosphere. The branch pipe 32 extends downward from the pipe 26 for opening, to the atmosphere, and further, is bent and extends Mona the pipe 26 for opening to the atmosphere. The other end portion of the branch pipe 32 is an opening 32A that opens to the atmosphere. Further, a compressor 34 is provided at this other end portion of the branch pipe 32, and compressed air is supplied from the compressor 34 to the branch pipe 32.

Here, the temperature sensor 36, the opening/closing valve 28, the pressure adjusting valve 30, the compressor 34, and the cooling device 24 that is described later are electrically connected to an ECU (Electronic Control Unit) 38 that is a control section, and are controlled by the ECU 38.

The bag-shaped member 16 and the cooling device 24 are described next. As shown in FIG 2 and FIG 3, the bag-shaped member 16 is mounted to the upper wall of the fuel tank 10. Further, the bag-shaped member 16 is formed of a resin material that is expandable and contractible, and is structured so as to be able to inflate or deflate in accordance with the height of the liquid surface of the fuel GS that is accommodated in the fuel tank 10. Concretely, as shown in FIG 2, in a case in which the liquid surface of the fuel GS is at a high position, the bag-shaped member 16 is deflated. Further, due to a signal being transmitted from the ECU 38 to the pressure adjusting valve 30 and the pressure adjusting valve 30 being opened, the pressure at the interior of the bag-shaped member 16 drops and the bag-shaped member 16 deflates. At this time, the bag-shaped member 16 contacts the liquid surface of the fuel GS at least at the region between the introducing pipe 20 and the lead-out pipe 22.

Here, the deflation limiting members 18, that limit the bag-shaped member 16 from deflating to less than a predetermined size, are provided at the fuel tank 10. The deflation limiting members 18 are provided at the region between the introducing pipe 20 and the lead-out pipe 22, and project-out downwardly from the upper wall of the fuel tank 10. Further, this is a structure in which the deflation limiting members 18 contact the bag-shaped member 16 in a state in which the fuel GS has been filled-in up to the full-tank liquid level. Due thereto, the bag-shaped member 16 does not deflate further at least at the region between the introducing pipe 20 and the lead-out pipe 22.

Figure 3:
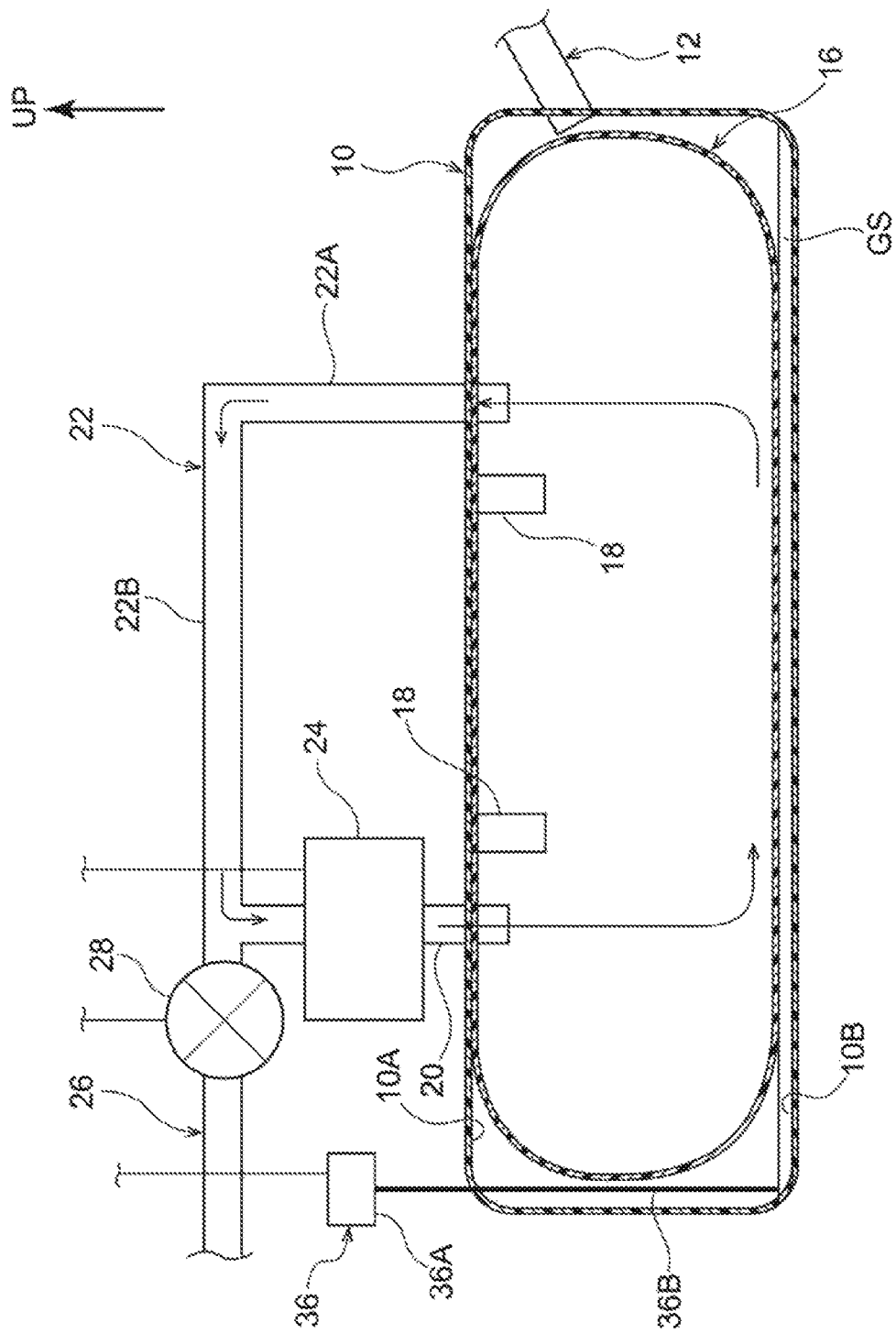
FIG 3 is a drawing that corresponds to FIG 2 and shows a state in which the bag-shaped member is inflated.

On the other hand, as shown in FIG 3, in the state in which the amount of fuel GS has decreased and the liquid level has dropped, the bag-shaped member 16 is inflated in accordance with the height of the liquid surface of the fuel GS. Concretely, due to a signal being transmitted from the ECU 38 to the compressor 34 and compressed air being sent to the bag-shaped member 16, the bag-shaped member 16 is inflated (see FIG 1). Further, the bag-shaped member 16 contacts the liquid surface of the fuel GS. In this way, due to the bag-shaped member 16 being inflated or deflated in accordance with the height of the liquid surface of the fuel GS, the state of contact of the bag-shaped member 16 and the liquid surface of the fuel GS is maintained.

The processes of lowering the temperature within the fuel tank 10 are described next.

The temperature of the fuel GS accommodated within the fuel tank 10 is detected by the temperature sensor 36. If there is a state in which the temperature of the fuel GS accommodated within the fuel tank 10 is low, the cooling device 24 does not operate. On the other hand, in a case in which the temperature of the fuel GS becomes higher than a predetermined temperature e.g., 30° C.), a signal is transmitted from the ECU 38 to the cooling, device 24, and the cooling device 24 is operated. At this time, the cooling device 24 operates regardless of the state of the bag-shaped member 16. Namely, the cooling device 24 operates regardless of whether the bag-shaped member 16 is deflated or the bag-shaped member 16 is inflated. Here, as an example, explanation will be given with reference to FIG 2.

Due to the cooling device 24 operating, the air that flows within the introducing pipe 20 is cooled and becomes cooling wind and is introduced into the bag-shaped member 16. Then, due to convection, the low-temperature air that has been introduced into the bag-shaped member 16 falls and moves along the inner surface of the bag-shaped member 16. Here, because the bag-shaped member 16 and the liquid surface of the fuel GS contact one another, the cooling wind flows in the direction of the arrows at the interior of the bag-shaped member 16 while taking heat away from the fuel GS.

The temperature of the cooling wind becomes high due to the cooling wind taking heat away from the fuel GS. The air, that rises as the temperature becomes high and that reaches a vicinity of the lead-out pipe 22, moves upward through the lead-out pipe 22.

The air that flows-through the lead-out pipe 22 reaches the portion connected with the introducing pipe 20. Here, in the present embodiment, at the time of cooling the fuel tank 10, the opening/closing valve 28 is controlled so as to be closed. Therefore, the high-temperature air flows from the lead-out pipe 22 into the introducing pipe 20, and again passes-through the cooling wind introducing section 21 and is cooled. Thereafter, the air is introduced into the bag-shaped member 16 from the introducing pipe 20, and moves through the interior of the bag-shaped member 16 while taking heat away from the fuel GS.

In this way, due to the air of the introducing pipe 20 being cooled and being circulated, the heat at the interior of the fuel tank 10 is taken, and the temperature is lowered. Further, when the temperature of the fuel GS that is detected by the temperature sensor 36 becomes lower than the predetermined temperature, the cooling device 24 is stopped by the ECU 38. Further, the opening/closing valve 28 is opened. Note that the same holds for a case in which the bag-shaped member 16 is inflated as shown in FIG 3, and, due to the cooling wind being circulated, heat is taken away from the fuel GS and the temperature of the fuel tank 10 interior can be lowered.

Note that there may be a structure in which, even in a state in which the engine is stopped such as at the time of refueling the fuel GS or the like, cooling wind is sent into the bag-shaped member 16 in a case in which the temperature of the fuel GS that is detected by the temperature sensor 36 becomes higher than the predetermined temperature. Namely, even in a state in which the engine is stopped, if electricity is supplied from an accessory battery or the like, in a case in which the temperature of the fuel GS becomes higher than the predetermined temperature, the cooling device 24 can be operated and cooling wind can be introduced into the bag-shaped member 16. Due thereto, the pressure within the fuel tank 10 decreases, and it becomes easy to fill fuel into the fuel tank 10 from the filler pipe 12 at the time of refueling. Namely, the operational efficiency of the refueling can be improved.

(Operation and Effects)

Operation and effects of the fuel tank structure relating to the present embodiment are described next.

In the present embodiment, when the temperature within the fuel tank 10 rises, cooling wind is introduced into the interior of the bag-shaped member 16 by the cooling device 24 that structures the cooling wind introducing section 21, and heat of the fuel GS is taken away from the portion that contacts the fuel GS. Due thereto, the temperature of the fuel GS can be lowered, and the amount of evaporated fuel can be reduced. As a result, a rise in the pressure of the fuel tank 10 interior can be suppressed. In particular, in the present embodiment, because air is cooled by a Peltier element, the cooling efficiency is high and the temperature of the fuel GS can be lowered in a short time, as compared with a structure that uses ordinary-temperature air as the cooling wind.

Further, in the present embodiment, at the time of cooling the fuel tank 10, the opening/closing valve 28 is closed, and the cooling wind is circulated. Due thereto, the temperature of the interior of the bag-shaped member 16 can be maintained at a low temperature, and the fuel tank 10 can be cooled effectively. Namely, a rise in the pressure of the fuel tank 10 interior can be suppressed effectively.

By controlling a rise in the pressure of the fuel tank 10 interior as described above, there is no need to provide a member for adsorbing evaporated fuel, such as a canister or the like. Namely, when the pressure adjusting valve 30 is opened in a state in which the pressure of the fuel tank 10 interior is high, evaporated fuel is discharged-out into the atmosphere, and therefore, a canister for adsorbing this evaporated fuel is needed. In contrast, in the present embodiment, by lowering the temperature of the fuel GS and suppressing a rise in the pressure of the fuel tank 10, the amount of evaporated fuel within the fuel tank 10 decreases, and therefore, a canister is unnecessary.

Further, in a case in which a canister is provided, there is the need to suck the evaporated fuel, that has been adsorbed by the canister, by negative pressure from the intake manifold in order to clean the canister. Here, if evaporated fuel is sucked by negative pressure from the intake manifold, the pumping loss increases, and therefore, it is difficult to improve the fuel efficiency. On the other hand, in the present embodiment, there is no need to provide a canister, and there is also no need to suck evaporated fuel, and therefore, the pumping loss can be suppressed. As a result, the fuel efficiency can be improved while discharging of evaporated fuel is suppressed.

Moreover, in the present embodiment, by inflating or deflating the bag-shaped member 16 in accordance with the height of the liquid surface of the fuel GS, the state of contact between the bag-shaped member 16 and the liquid surface is maintained. Due thereto, at the time of cooling the fuel GS, heat can be quickly taken away from the fuel GS. Namely, in a structure in which the liquid surface of the fuel GS and the bag-shaped member 16 are apart from one another, the cooling efficiency is lower than a case in which the bag-shaped member 16 contacts the liquid surface. In contrast, by maintaining the state of contact of the bag-shaped member 16 and the liquid surface, a decrease in the cooling efficiency can be suppressed, and the temperature of the fuel GS can be lowered at an early stage. Further, by maintaining the state of contact of the bag-shaped member 16 and the liquid surface, the generating of evaporated fuel is suppressed, and a rise in the pressure of the fuel tank 10 interior can be suppressed.

Further, in the present embodiment, collapsing of the bag-shaped member 16 is suppressed by the deflation limiting members 18. Due thereto, the flow path of the cooling wind can be ensured regardless of the height of the liquid surface of the fuel GS, and the performance of cooling the fuel GS can be maintained good.

<Second Embodiment>

A fuel tank structure relating to a second embodiment is described next with reference to FIG 4. Note that structures that are similar to those of the first embodiment are denoted by the same reference numerals, and description thereof is omitted as appropriate.

Figure 4:
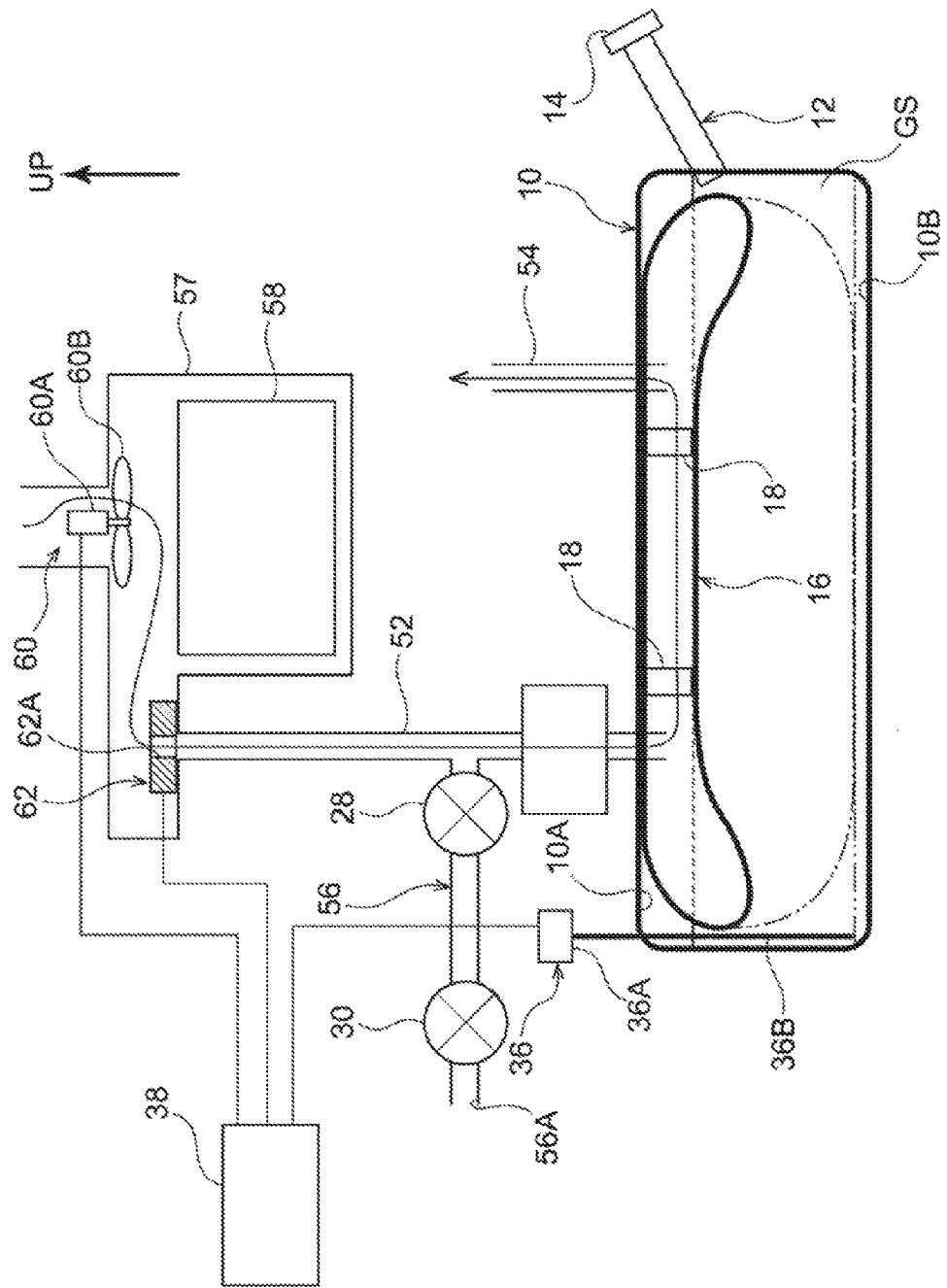
FIG 4 is a drawing that schematically shows the overall structure of a fuel tank structure relating to a second embodiment.

As shown in FIG 4, in the fuel tank structure relating to the present embodiment, an introducing pipe 52 and a lead-out pipe 54 are connected to the ceiling portion 10A of the fuel tank 10. The introducing pipe 52 is a pipe body for introducing air into the bag-shaped member 16, and extends it the vertical direction. Further, the lower end portion of the introducing pipe 52 is disposed at the interior of the fuel tank 10. On the other hand, the upper end portion of the introducing pipe 52 is connected to a battery chamber 57 that serves as a cooling wind introducing section.

Here, a battery 58 is installed in the battery chamber 57. A blower 60 for cooling the battery 58 is provided above the battery 58. The blower 60 is structured to include a motor 60A and rotating vanes 60B. Further, due to electric current being supplied to the motor 60A and the motor 60A being driven, the rotating vanes 60B rotate, and air (cooling wind) is sent to the battery 58, and the battery 58 is thereby cooled.

Further, a flow rate adjusting member 62 is provided at the portion where the introducing pipe 52 is connected at the battery chamber 57. In the present embodiment, as an example, the flow rate adjusting member 62 that is substantially cylindrical and is flat is provided, and a through-hole 62A, whose diameter is smaller than that of the introducing pipe 52, is formed in the central portion of this flow rate adjusting member 62. This is a structure in which, due to this through-hole 62A and the introducing pipe 52 communicating with one another, the air that is sent-out from the blower 60 can be introduced into the introducing pipe 52.

Moreover, the flow rate adjusting member 62 is structured so as to be movable in a direction that is orthogonal to the axial direction of the introducing pipe 52 (the vertical direction), by a mechanism such as a rack-and-pinion or the like for example. Therefore, this is a structure in which, by moving the flow rate adjusting member 62, the surface area at which the introducing pipe 52 and the through-hole 62A overlap one another in the axial direction changes, and the flow rate of the air that is introduced from the battery chamber 57 into the introducing pipe 52 can be adjusted.

One end portion of a pipe 56 for opening to the atmosphere is connected to the introducing pipe 52. The pipe 56 for opening to the atmosphere extends horizontally, and an opening 56A that opens to the atmosphere is formed at the other end portion of the pipe 56 for opening to the atmosphere. Further, the pressure adjusting valve 30 and the opening/closing valve 28 are provided at the pipe 56 for opening to the atmosphere, in that order from the opening 56A side. Note that the opening/closing valve 28, the pressure adjusting valve 30, the temperature sensor 36, the flow rate adjusting member 62, and the motor 60A of the blower 60 are respectively electrically connected to the ECU 38.

(Operation and Effects)

Operation and effects of the fuel tank structure relating to the present embodiment are described next.

In the present embodiment, in a case in which the temperature of the fuel GS that is detected by the temperature sensor 36 becomes higher than at predetermined temperature (e.g., 30° C.), a signal is transmitted from the ECU 38 to the flow rate adjusting member 62. Due thereto, air that is sent-out from the blower 60 is introduced into the introducing pipe 52 via the through-hole 62A of the flow rate adjusting member 62. At this time, the ECU 38 adjusts the position of the flow rate adjusting member 62 such that the flow rate adjusting member 62 is coaxial with the introducing pipe 52. Due thereto, air from the blower 60 is introduced into the introducing pipe 52.

The air that is introduced into the introducing pipe 52 moves down the introducing pipe 52 and is introduced into the bag-shaped member 16. Here, because the opening/closing valve 28 is closed by the ECU 38, air does not flow into the pipe 56 for opening to the atmosphere.

Due to convection, the air that has been introduced into the bag-shaped member 16 falls and moves along the inner surface of the bag-shaped member 16. Here, because the Bag-shaped member 16 and the liquid surface of the fuel GS contact one another, the air flows in the direction of the arrow at the interior of the bag-shaped member 16 while taking heat away from the fuel GS.

The air, whose temperature has become high by taking heat of the fuel GS away, rises and is led-out into the lead-out pipe 54, and passes-through this lead-out pipe 54 and is released into the atmosphere. Namely, the present embodiment is a structure that does not circulate air. Further, because air is not cooled by using, a Peltier element or the like, there is no need to consider cooling of the heat-exhausting side of the Peltier element, or the like.

When the temperature that is detected by the temperature sensor 36 becomes lower than the predetermined temperature, the ECU 38 moves the flow rate adjusting member 62 and closes the opening at the upper end side of the introducing pipe 52. Namely, the communicated state of the battery chamber 57 and the introducing pipe 52 is cancelled. Due thereto, the flow of air stops, and cooling of the fuel GS stops.

In this way, by sending air into the bag-shaped member 16 in the same way as in the first embodiment, heat is taken away from the contacting portion of the bag-shaped member 16 and the liquid surface and the temperature of the fuel GS can be lowered. Further in the present embodiment, because air is introduced-in by utilizing the blower 60 that cools the battery 58, there is no need to provide a separate cooling device, and the number of parts can be decreased. Other operations are similar to those of the first embodiment.

Although a first embodiment and a second embodiment of the present invention have been described above, the present invention is not limited to the above-described structures and can, of course, be implemented in various forms other than the above-described structures within a scope that does not depart from the gist thereof. For example, the above-described embodiments are structured such that the detecting portion 36B of the temperature sensor 36 extends all the way to the bottom portion of the fuel tank 10 and senses the temperature of the accommodated fuel GS, but embodiments are not limited to this. For example, the first embodiment describes a device that is equipped with a Peltier element as the cooling device 24, but embodiments are not limited to this. There may be a structure in which air is cooled by being passed through a water pipe of cooling water at the interior of the introducing pipe.

Moreover, in the above-described embodiments, two of the deflation limiting members 18 are disposed at the interior of the fuel tank 10, but embodiments are not limited to this. For example, three or more o the deflation limiting members 18 may be provided. Further, there may be a structure in which the deflation limiting members 18 are not provided. In this case, by adjusting the height of the liquid surface of the fuel GS at the time when the tank is full, a flow path of air can be ensured at the interior of the bag-shaped member 16 even if the deflation limiting members 18 are not provided.

Further, the shape of the bag-shaped member 16 as well is not particularly limited, and another shape may be employed. For example, a bag-shaped member that is tubular and whose outer peripheral surface is bellows-shaped and that can expand and deflate vertically, may be used.

What is claimed is:

1. A fuel tank structure comprising:
   a fuel tank that is installed in an automobile and that accommodates fuel;
   a bag-shaped member that is fixed to a ceiling portion of an interior of the fuel tank, a state of contact of the bag-shaped member with a liquid surface of fuel accommodated in the fuel tank being maintained due to the bag-shaped member inflating or deflating in accordance with a height of the liquid surface;
   a temperature sensor that detects a temperature of the fuel or evaporated fuel that is within the fuel tank; and
   a cooling wind introducing section that introduces cooled air into an interior of the bag-shaped member in a case in which the temperature of the fuel or the evaporated fuel detected by the temperature sensor is higher than a predetermined temperature, wherein
   the cooling wind introducing section includes an introducing pipe that introduces the cooled air into the bag-shaped member, and a cooling device that cools the cooled air that flows through the introducing pipe.

2. The fuel tank structure of claim 1, wherein the cooling wind introducing section further includes:
   a lead-out pipe connected to the bag-shaped member, the lead-out pipe circulating the cooled air by leading the cooled air, that has been introduced into the bag-shaped member from the introducing pipe, out of the bag-shaped member and back to the introducing pipe.

3. The fuel tank structure of claim 1, further comprising a deflation limiting member, that limits the bag-shaped member from deflating to less than a predetermined size, provided at the fuel tank.

4. The fuel tank structure of claim 1, wherein:
   the cooling device cools the cooled air in the case in which the temperature of the fuel or the evaporated fuel detected by the temperature sensor is higher than the predetermined temperature, and
   the cooling device does not cool the cooled air in a case in which the temperature of the fuel or the evaporated fuel detected by the temperature sensor is not higher than the predetermined temperature.

5. A fuel tank structure comprising:
   a fuel tank that is installed in an automobile and that accommodates fuel;
   a bag-shaped member that is fixed to a ceiling portion of an interior of the fuel tank, a state of contact of the bag-shaped member with a liquid surface of fuel accommodated in the fuel tank being maintained due to the bag-shaped member inflating or deflating in accordance with a height of the liquid surface;
   a temperature sensor that detects a temperature of the fuel or evaporated fuel that is within the fuel tank; and
   a cooling wind introducing section that introduces cooling air into an interior of the bag-shaped member in a case in which the temperature of the fuel or the evaporated fuel detected by the temperature sensor is higher than a predetermined temperature, wherein
   the cooling wind introducing section does not introduce the cooling air into the interior of the bag-shaped member in a case in which the temperature of the fuel or the evaporated fuel detected by the temperature sensor is not higher than the predetermined temperature.

6. The fuel tank structure of claim 5, wherein the cooling wind introducing section further includes:
   an introducing pipe that introduces the cooling air into the bag-shaped member, and
   a cooling device that cools the cooling air that flows through the introducing pipe.

7. The fuel tank structure of claim 6, wherein the cooling wind introducing section further includes:
   a lead-out pipe connected to the bag-shaped member, the lead-out pipe circulating the cooling air by leading the cooling air, that has been introduced into the bag-shaped member from the introducing pipe, out of the bag-shaped member and back to the introducing pipe.

8. The fuel tank structure of claim 5, further comprising a deflation limiting member, that limits the bag-shaped member from deflating to less than a predetermined size, provided at the fuel tank.

* * * * *